US012672860B2

(12) United States Patent
Park

(10) Patent No.: US 12,672,860 B2
(45) Date of Patent: Jul. 7, 2026

(54) MEDICAL SNARE DEVICE

(71) Applicant: SAMSUNG LIFE PUBLIC WELFARE FOUNDATION, Seoul (KR)

(72) Inventor: Hong Suk Park, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 264 days.

(21) Appl. No.: 18/250,272

(22) PCT Filed: Jun. 3, 2021

(86) PCT No.: PCT/KR2021/006941
§ 371 (c)(1),
(2) Date: Apr. 24, 2023

(87) PCT Pub. No.: WO2022/092471
PCT Pub. Date: May 5, 2022

(65) Prior Publication Data
US 2023/0389910 A1 Dec. 7, 2023

(30) Foreign Application Priority Data
Oct. 28, 2020 (KR) ........................ 10-2020-0141566

(51) Int. Cl.
*A61B 17/00* (2006.01)
(52) U.S. Cl.
CPC .................. *A61B 17/00234* (2013.01); *A61B 2017/00358* (2013.01)

(58) Field of Classification Search
CPC ............ A61B 17/00234; A61B 17/221; A61B 17/32056; A61B 2017/00358; A61B 2017/2212; A61B 2017/2217
See application file for complete search history.

(56) References Cited

U.S. PATENT DOCUMENTS 4,471,777 A 9/1984 McCorkle, Jr.
9,808,270 B2 * 11/2017 Tah ...................... A61B 17/221
(Continued)

FOREIGN PATENT DOCUMENTS

JP 2004-130102 A 4/2004
KR 10-0610953 B1 8/2006
(Continued)

OTHER PUBLICATIONS

Extended European Search Report issued Jul. 24, 2024 in European Patent Application No. 21886472.6, 9 pages.
(Continued)

*Primary Examiner* — Anh T Dang
(74) *Attorney, Agent, or Firm* — Oblon, McClelland, Maier & Neustadt, L.L.P.

(57) ABSTRACT
An embodiment of the present disclosure provides a medical snare device including a main body unit that is open on both sides and has a hollow interior, a guide unit that is relatively movable inside the main body unit and has a hollow interior, and a snare unit including a capture unit having a capture hole unit formed therein, and a plurality of support units that are relatively movable inside the guide unit and connected to the capture unit, wherein the plurality of support units are connected to preset points of the capture unit, respectively.

6 Claims, 7 Drawing Sheets

1

(56) References Cited

U.S. PATENT DOCUMENTS

| | | | |
|---|---|---|---|
| 2007/0027456 A1 * | 2/2007 | Gartner ............... | A61B 17/221 |
| | | | 606/113 |
| 2009/0112244 A1 | 4/2009 | Freudenthal | |
| 2013/0296878 A1 | 11/2013 | Shin | |
| 2014/0155980 A1 | 6/2014 | Turjman et al. | |
| 2014/0378988 A1 | 12/2014 | Raybin et al. | |
| 2015/0173783 A1 | 6/2015 | Tah et al. | |
| 2015/0230820 A1 | 8/2015 | Turjman et al. | |
| 2016/0354099 A1 | 12/2016 | Turjman et al. | |
| 2017/0007278 A1 | 1/2017 | Kramann | |
| 2017/0049472 A1 * | 2/2017 | Uihlein ............ | A61B 17/32056 |
| 2017/0143357 A1 | 5/2017 | Uihlein | |
| 2019/0366082 A1 | 12/2019 | Schmidt et al. | |
| 2020/0229841 A1 | 7/2020 | Motai | |

FOREIGN PATENT DOCUMENTS

| | | |
|---|---|---|
| KR | 10-2012-0086233 A | 8/2012 |
| KR | 10-2019-0012946 A | 2/2019 |
| KR | 10-2020-0030766 A | 3/2020 |
| WO | WO 85/04320 A1 | 10/1985 |
| WO | WO 2014/008460 A2 | 1/2014 |
| WO | WO 2014/008460 A3 | 1/2014 |
| WO | WO 2015/100045 A1 | 7/2015 |
| WO | WO 2015/100045 A8 | 7/2015 |
| WO | WO 2019/178543 A1 | 9/2019 |

OTHER PUBLICATIONS

International Search Report issued Sep. 14, 2021 in PCT/KR2021/006941 filed on Jun. 3, 2021, 2 pages.

Korean Office Action issued Dec. 14, 2022 in Korean Application No. 10-2020-0141566 filed on Oct. 28, 2020, 10 pages (with Machine Generated English Translation).

Office Action issued in European Patent Application No. 21886472.6 on Sep. 5, 2025.

* cited by examiner

MEDICAL SNARE DEVICE

TECHNICAL FIELD

Embodiments of the present disclosure relate to a medical snare device, and more particularly, to a medical snare device capable of easily removing a foreign substance or an instrument temporarily inserted in a blood vessel or a gastrointestinal tract.

BACKGROUND ART

In general, a snare is used to easily remove a foreign substance or an instrument temporarily inserted in a blood vessel or a gastrointestinal tract during an interventional procedure.

A snare may be introduced into the body of a subject by using, as a guide, a catheter already inserted into the body of the subject. In such a snare, a wire may be inserted into a tube made of a flexible insulating material, and an operating mechanism may be connected to one end of the wire.

A trap is formed at the other end of the wire in the snare, and by manipulating the operating mechanism to push and pull the wire, the trap is drawn in and out of the end of the tube.

When the trap is drawn out of the end of the tube, the size of the inner region of the trap may increase, and when the trap is withdrawn into the end of the tube, the size of the inner region of the trap may decrease due to the diameter of the tube.

In the snare in the art, it is difficult to capture a target such as a foreign substance or a temporarily inserted instrument because the tube has no directionality, or even when the tube has directionality by being bent, it is difficult to precisely adjust the directionality, and even when the target is captured under two-dimensional fluoroscopic guidance in a three-dimensional situation, the target is captured incompletely in most cases, and may be missed in a process of removing the same.

The related art of the present disclosure is disclosed in Korean Patent Publication No. 10-2012-0086233, published on Aug. 2, 2012 and entitled "Medical snare".

DISCLOSURE

Technical Problem

The present disclosure has been made in an effort to improve the above-described issues, and provides a medical snare device including a plurality of support units each connected to a capture unit so as to prevent a movement in a longitudinal direction, and easily remove a foreign substance or an instrument temporarily inserted in a blood vessel or a gastrointestinal tract.

However, this objective is merely illustrative, and the scope of the present disclosure is not limited thereto.

Technical Solution

According to embodiments of the present disclosure, provided is a medical snare device including: a main body unit that is open on both sides and has a hollow interior; a guide unit that is relatively movable inside the main body unit and has a hollow interior; and a snare unit including a capture unit having a capture hole unit formed therein, and a plurality of support units that are relatively movable inside the guide unit and connected to the capture unit, wherein the plurality of support units are connected to preset points of the capture unit, respectively.

In the present disclosure, the plurality of support units may be arranged to face each other with respect to a center of the capture hole unit.

In the present disclosure, the plurality of support units may be integrally formed in a preset section.

In the present disclosure, the guide unit may include a plurality of guide bodies that provide moving paths of the plurality of support units, respectively.

In the present disclosure, the plurality of guide bodies may be integrally formed in a preset section.

In the present disclosure, the main body unit may be formed of a polymer material.

In the present disclosure, the plurality of support units may be formed of a metal or polymer material.

Other aspects, features, and advantages other than those described above will be apparent from the following drawings, claims, and detailed description.

Advantageous Effects

A medical snare device according to embodiments of the present disclosure includes a plurality of support units each connected to a preset position on a capture unit, such that the capture unit is stably positioned outside an object, such as a foreign substance or an instrument that has been temporarily inserted, and the object is accurately captured.

In addition, the capture unit is formed in a structure in which a plurality of arcs are connected to each other such that the size of the capture unit may be adjusted, for example, may be reduced even inside a main body unit or a guide unit having a relatively small diameter, and even when the size of the entire capture unit is reduced, its circular shape may be maintained due to the plurality of arcs, and thus, a shape necessary for capturing an object may be implemented.

However, the scope of the present disclosure is not limited by these effects.

BEST MODE

Figure 1:
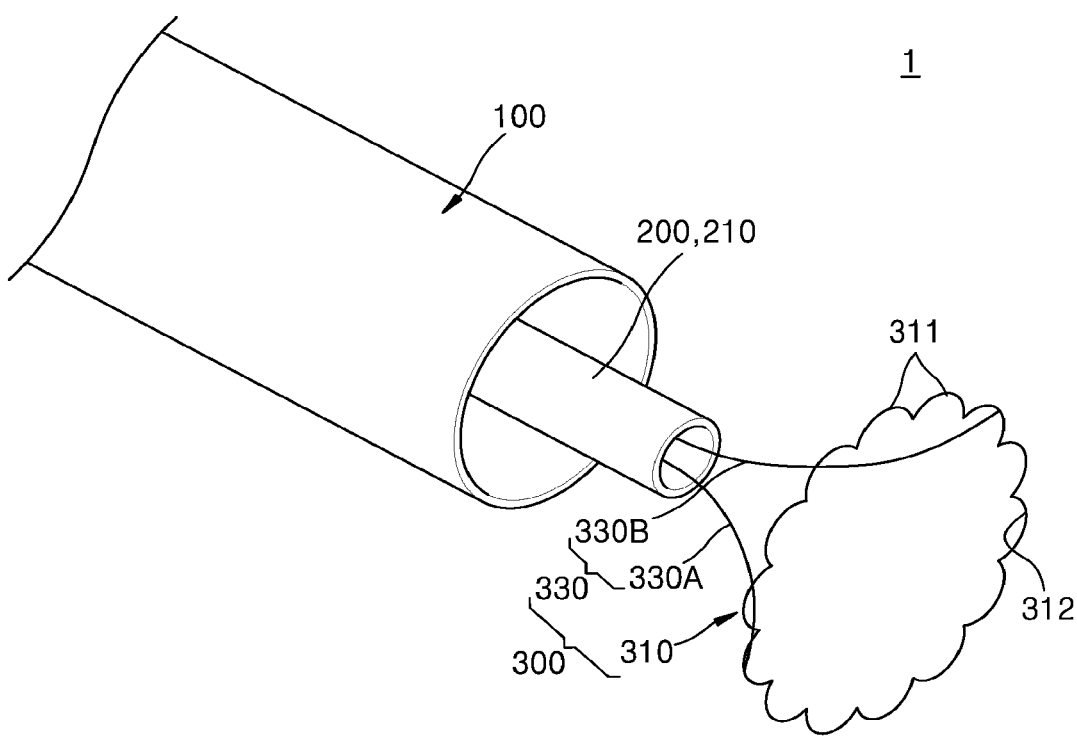
FIG. 1 is a partial perspective view illustrating a medical snare device according to an embodiment of the present disclosure.

As the present disclosure allows for various changes and numerous embodiments, particular embodiments will be illustrated in the drawings and described in detail. The effects and features of the present disclosure and methods of achieving them will become clear with reference to the embodiments described in detail below with the drawings. However, the present disclosure is not limited to the embodiments disclosed below, and may be implemented in various forms.

Hereinafter, embodiments of the present disclosure will be described in detail with reference to the accompanying drawings, and the same or corresponding components will be denoted by the same reference numerals when described with reference to the accompanying drawings, and thus, their descriptions that are already provided will be omitted.

In the following embodiments, terms such as "first," "second," etc., are used only to distinguish one component from another, and such components must not be limited by these terms.

In the following embodiments, the singular expression also includes the plural meaning as long as it is not inconsistent with the context.

In the following embodiments, the terms "comprises," "includes," "has", and the like used herein specify the presence of stated features or components, but do not preclude the presence or addition of one or more other features or components.

In the following embodiments, when a layer, region, or component is referred to as being "on" another layer, region, or component, it may be directly or indirectly on the other layer, region, or component, that is, one or more intervening layers, regions, or components may be present therebetween.

For ease of description, the magnitude of components in the drawings may be exaggerated or reduced. For example, each component in the drawings is illustrated to have an arbitrary size and thickness for ease of description, and thus the present disclosure is not limited to the drawings.

When a certain embodiment may be differently implemented, particular operations may be performed differently from the sequence described herein. For example, two processes, which are successively described herein, may be substantially simultaneously performed, or may be performed in a process sequence opposite to a described process sequence.

In the following embodiments, when a layer, region, or component is referred to as being connected to another layer, region, or component, they may be directly connected to each other, or may be indirectly connected to each other with still another layer, region, or component therebetween. In the present specification, for example, when a layer, region, or component is referred to as being electrically connected to another layer, region, or component, they may be directly electrically connected to each other, or may be indirectly electrically connected to each other with still another layer, region, or component therebetween.

Figure 2:
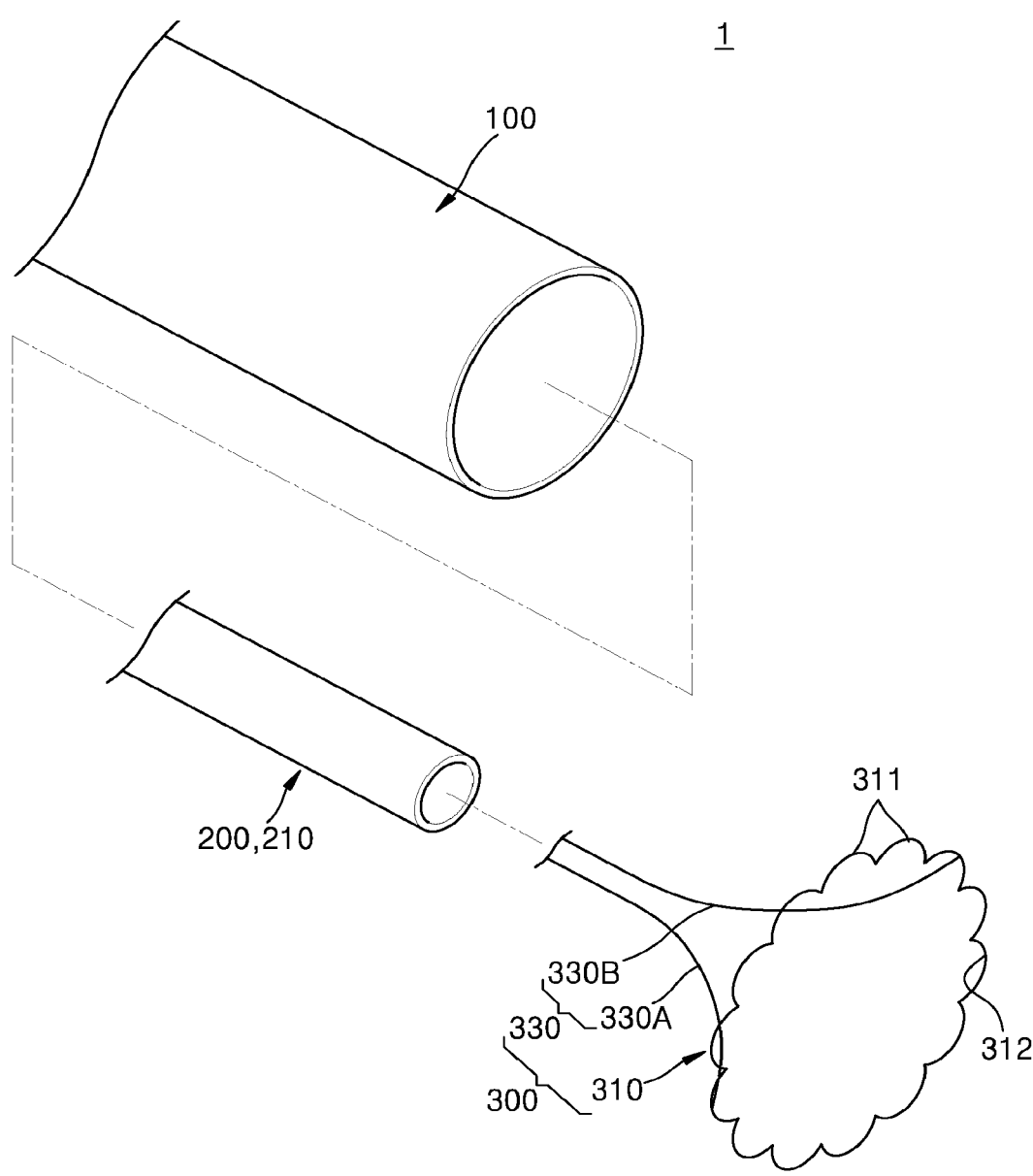
FIG. 2 is an exploded perspective view illustrating a medical snare device according to an embodiment of the present disclosure.
Figure 3:
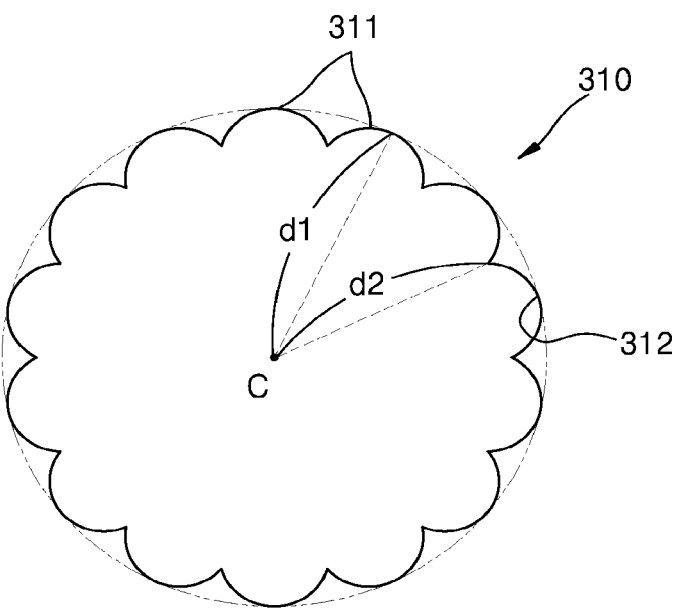
FIG. 3 is a plan view illustrating a capture unit according to an embodiment of the present disclosure.
Figure 4:
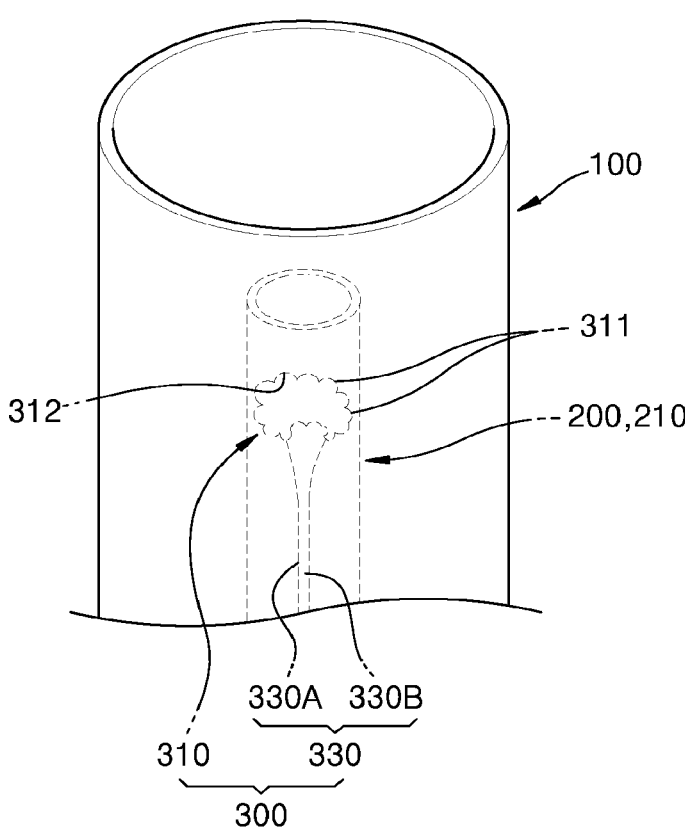
FIG. 4 is a diagram illustrating a state in which a snare unit is located inside a main body unit, according to an embodiment of the present disclosure.
Figure 5:
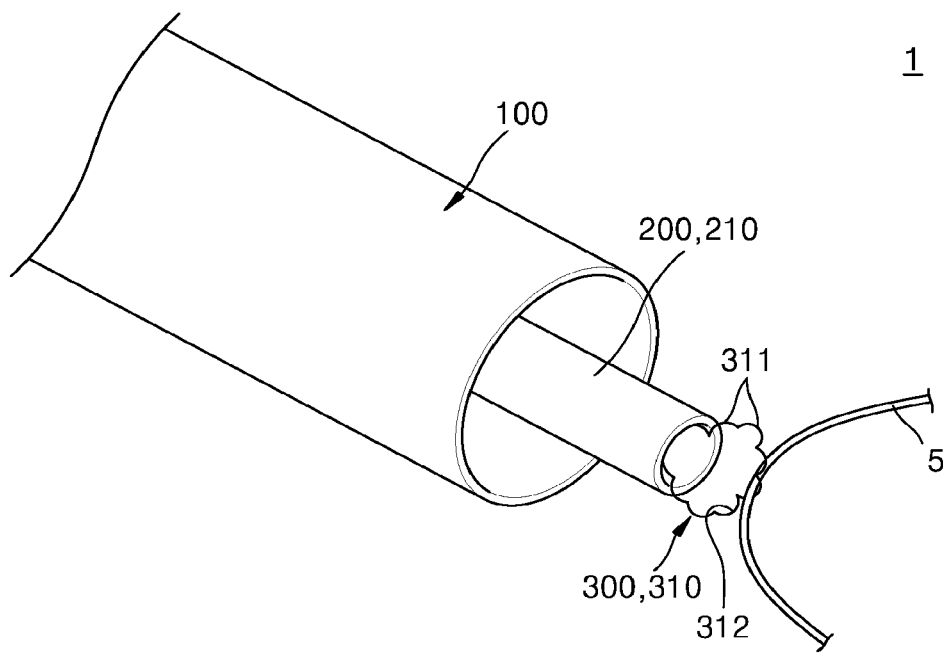
FIG. 5 is a diagram illustrating a state of use of a medical snare device according to an embodiment of the present disclosure.

FIG. 1 is a partial perspective view illustrating a medical snare device according to an embodiment of the present disclosure. FIG. 2 is an exploded perspective view illustrating a medical snare device according to an embodiment of the present disclosure. FIG. 3 is a plan view illustrating a capture unit according to an embodiment of the present disclosure. FIG. 4 is a diagram illustrating a state in which a snare unit is located inside a main body unit, according to an embodiment of the present disclosure. FIG. 5 is a diagram illustrating a state of use of a medical snare device according to an embodiment of the present disclosure.

Referring to FIGS. 1 to 5, a medical snare device 1 according to an embodiment of the present disclosure may include a main body unit 100, a guide unit 200, and a snare unit 300.

Referring to FIGS. 1, 2, 4, and 5, the main body unit 100 according to an embodiment of the present disclosure may be formed in a cylindrical shape with open ends and a hollow interior.

The main body unit 100 according to an embodiment of the present disclosure may extend along a central axis in the longitudinal direction, and may be formed to have a preset cross-sectional area to be insertable into a blood vessel or a gastrointestinal tract.

In the present disclosure, the main body unit 100 may be formed in a cylindrical shape, but is not limited thereto, and various modifications are possible within the technical spirit in which the guide unit 200 and the snare unit 300 to be described below may be arranged to be movable in the longitudinal direction inside the main body unit 100.

The main body unit 100 according to an embodiment of the present disclosure may be formed such that the area of a cross section with respect to the central axis in the longitudinal direction is greater than that of the guide unit 200.

As such, a user may stably capture an object 5 to be removed by grasping the main body unit 100, moving the main body unit 100 to the position of the object 5, moving the guide unit 200 inside the main body unit 100 at the position, and moving the snare unit 300 to be described below inside the guide unit 200.

Referring to FIGS. 1, 2, 4, and 5, the main body unit 100 according to an embodiment of the present disclosure may be formed of a polymer material to be flexibly movable in a blood vessel or a gastrointestinal tract.

Referring to FIGS. 1, 2, 4, and 5, the main body unit 100 according to an embodiment of the present disclosure may have a diameter of 5 fr to 15 fr. 5 fr to 15 fr may mean 1.67 mm to 5 mm.

The length of the main body unit 100 according to an embodiment of the present disclosure may be variously modified within a preset length considering a blood vessel or a gastrointestinal tract into which the main body unit 100 is to be inserted, in a range of 10 cm to 200 cm.

Referring to FIGS. 1, 2, 4, 5, and 6, the guide unit 200 according to an embodiment of the present disclosure may be formed to be relatively movable inside the main body unit 100 and have a hollow interior.

Referring to FIG. 2, the guide unit 200 according to an embodiment of the present disclosure may be formed in a cylindrical shape, and may be formed such that the area of a cross section with respect to the central axis in the longitudinal direction is less than that of the main body unit 100.

As such, the guide unit 200 and the main body unit 100 are able to move relatively to each other, and the user may move the guide unit 200 in a state in which the main body unit 100 is fixed in position, and may move the main body unit 100 in a state in which the guide unit 200 is fixed in position.

That is, relative movement between the guide unit 200 and the main body unit 100 according to an embodiment of the present disclosure may allow the user to move the main body unit 100 to a region in which the object 5, such as a foreign substance or an instrument (e.g., an inferior vena cava filter or a stent) temporarily inserted in a blood vessel or a gastrointestinal tract, is located, then discharge the guide unit 200 from the inside of the main body unit 100, and stably capture and remove the object 5 through the snare unit 300 that is movable inside the guide unit 200.

The guide unit 200 according to an embodiment of the present disclosure may be formed of a metal or polymer material, have a preset rigidity, and maintain a fixed shape inside the main body unit 100.

As such, the snare unit 300 may be stably fixed in position inside the guide unit 200, and the guide unit 200 may move to the position of the object 5 to surround the object 5 with the snare unit 300, and then remove the object 5 from a blood vessel or a gastrointestinal tract.

Referring to FIGS. 1 to 5, the snare unit 300 according to an embodiment of the present disclosure may be movable inside the guide unit 200, and may include a capture unit 310 and support units 330, 330A, and 330B.

The snare unit 300 according to an embodiment of the present disclosure may be formed of a steel material or a polymer material, and may have a diameter of 5 mm to 40 mm.

Referring to FIGS. 4 and 5, the snare unit 300 according to an embodiment of the present disclosure may be formed to be movable inside the main body unit 100, and extend to a length corresponding to the lengths of the main body unit 100 and the guide unit 200.

Referring to FIGS. 1 to 5, the capture unit 310 according to an embodiment of the present disclosure may have a capture hole unit 312 formed therein, and after the object is located inside the capture hole unit 312, the user may pull the snare unit 300 to stably remove the object 5.

Referring to FIG. 3, the capture unit 310 according to an embodiment of the present disclosure may be provided with a plurality of arcs 311, and both ends of each of the plurality of arcs 311 may be connected to both ends of other arcs 311, respectively.

Referring to FIG. 3, a circle may be formed by connecting the central points of the plurality of arcs 311 to each other with an imaginary line, and the radii of curvature of the plurality of arcs 311 may be less than the radius of curvature of a preset region of the circle formed by the imaginary line.

Referring to FIG. 3, a distance d2 between a center C of the capture unit 310 and each of both ends of each arc 311, which is the point at which different arcs 311 are connected to each other, may be less than a distance d1 between the center C of the capture unit 310 and the center point of each arc 311, that is, the circle formed by the imaginary line.

In other words, the distance between the points at which the plurality of arcs 311 may be connected to each other and the center of the capture hole unit 312 may be less than the distance between the center of each arcs 311 and the center of the capture hole unit 312.

As such, the capture unit 310 in which the plurality of arcs 311 may be connected to each other has a large circular shape, but even in a case in which the diameters of the main body unit 100 and the guide unit 200 are relatively small, and the support units 330, 330A, and 330B are pulled, the capture unit 310, particularly, the plurality of arcs 311 may maintain a circular shape as much as possible while being partially folded.

In other words, while the capture unit 310 in which the plurality of arcs 311 are connected to each other may maintain a capture region located outside the guide unit 200 in a substantially circular shape, the inner diameter of the capture unit 310 may be changed when the user pulls the snare unit 300.

As such, as the inner diameter of the snare unit 300, particularly, the capture unit 310 may decrease, the object 5, such as a foreign substance or an instrument temporarily inserted in a blood vessel or a gastrointestinal tract, may be gripped or clamped inside the capture unit 310.

In addition, the area of the capture region may be adjusted, and this configuration is also applicable to the main body unit 100 and the guide unit 200 having various diameters, in addition to those of a single specification.

Referring to FIGS. 1, 2, 4, and 5, the support units 330, 330A, and 330B according to an embodiment of the present disclosure may be capable of relative movement inside the guide unit 200, and may be connected to the capture unit 310. A plurality of support units 330, 330A and 330B may be provided, and may be connected to preset points of the capture unit 310, respectively.

The support units 330, 330A, and 330B according to an embodiment of the present disclosure may be formed of a steel material to have a preset strength, and as the strength is secured, may stably move the snare unit 300 connected to the support units 330, 330A, and 330B to the position of the object 5.

Referring to FIGS. 1 and 2, the plurality of support units 330, 330A, and 330B according to an embodiment of the present disclosure may be arranged to face each other with respect to the center of the capture hole unit 312.

Referring to FIG. 5, as the plurality of support units 330, 330A, and 330B are provided and connected to the capture unit 310, when the user tightens the snare unit 300 for capturing the object 5 by adjusting the angle and position of the snare unit 300, there is no movement in the longitudinal axis direction, thus, the object 5 may be stably captured, and the captured object 5 may be easily removed without missing it.

Referring to FIGS. 1, 2, 4, and 5, two support units 330, 330A, and 330B according to an embodiment of the present disclosure may be provided and respectively connected to positions that are symmetrical to each other with respect to the center of the capture hole unit 312 on the capture unit 310, but the present disclosure is not limited thereto, and various modifications are possible, for example, three or more support units may be provided within the technical spirit in which movement in the longitudinal axis direction is prevented when pulling the snare unit 300.

Hereinafter, the operation principle and effects of the medical snare device 1 according to an embodiment of the present disclosure as described above will be described.

Referring to FIGS. 1 to 5, the medical snare device 1 according to an embodiment of the present disclosure may include the main body unit 100, the guide unit 200, and the snare unit 300.

FIG. 5 illustrates a situation in which the medical snare device 1 is located in a blood vessel or a gastrointestinal tract, which is not illustrated in the drawings, and an object such as a foreign substance or a temporarily inserted instrument may be located inside the blood vessel or gastrointestinal tract.

Referring to FIG. 4, the user may grip the main body unit 100 in which the guide unit 200 and the snare unit 300 are located, and move the main body unit 100 to a preset position inside the blood vessel or gastrointestinal tract in which the object 5 is located.

Referring to FIG. 5, when the main body unit 100 is moved to a position close to the object 5 located inside the blood vessel or gastrointestinal tract, the user may pull the main body unit 100 backward (from the top to the bottom in FIG. 4) such that the guide unit 200 and the snare unit 300 may be exposed to the outside of the main body unit 100.

The guide unit 200 and the snare unit 300 arranged inside the guide unit 200 may be exposed to the outside of the main body unit 100, and the object 5 is positioned inside the snare unit 300, particularly, inside the capture unit 310 formed by connecting the plurality of arcs 311 to each other to form the capture hole unit 312.

Referring to FIG. 3, the distance d2 between the points at which the plurality of arcs 311 are connected to each other and the center of the capture hole unit 312 may be less than the distance d1 between the center of each arcs 311 and the center of the capture hole unit 312.

As such, the capture unit 310 in which the plurality of arcs 311 are connected to each other has a large circular shape as a whole when connecting the central points of the arcs 311, which are furthest from the center of the capture unit 310, to each other with an imaginary line, and when the support units 330, 330A, and 330B are pulled, even in a case in which the diameters of the main body unit 100 and the guide unit 200 are relatively small, the capture unit 310, particularly, the plurality of arcs 311 may partially buckle or fold but maintain the circular shape as possible.

In other words, while the capture unit 310 in which the plurality of arcs 311 are connected to each other may maintain a capture region located outside the guide unit 200 in a substantially circular shape, the inner diameter of the capture unit 310 may be changed when the user pulls the snare unit 300.

As such, as the inner diameter of the snare unit 300, particularly, the capture unit 310 decreases, the object 5, such as a foreign substance or an instrument temporarily inserted in a blood vessel or a gastrointestinal tract, may be gripped or clamped inside the capture unit 310.

In addition, a snare device having a size corresponding to the diameter of a blood vessel or a gastrointestinal tract is required, but the area of the capture region of the snare device according to the embodiments of the present disclosure is adjustable, and thus, the snare device is applicable to blood vessels or gastrointestinal tracts with various diameters, with the main body unit 100, the guide unit 200, and the snare unit 300 each having a single specification.

Referring to FIGS. 1, 2, 4, and 5, a plurality of support units 330, 330A, and 330B may be provided and connected to preset points on the capture unit 310, respectively. In detail, the support units 330, 330A, and 330B may be connected to positions facing each other with respect to the center of the capture hole unit 312.

As the plurality of supports 330, 330A, and 330B are provided and connected to the capture unit 310, the snare unit 300 may be stably moved, and movement in the longitudinal direction is prevented such that the capture unit 310 may be stably arranged outside the object 5 and easily capture the object 5.

In detail, when the user pulls the snare unit 300 to one side (from the right to the left in FIG. 5) in a state in which the guide unit 200 is fixed in position, the snare unit 300, particularly, a preset region of the capture unit 310 is inserted into the guide unit 200, and as the capture unit 310 is formed in a structure in which the plurality of arcs 311 are connected to each other, the capture unit 310 may be in a substantially circular shape even when it is folded to be inserted into the guide unit 200, and the size of the capture hole unit 312 is reduced, such that the object 5 is gripped, clamped, or caught.

Thereafter, the user may move the medical snare device 1 from the inside of the blood vessel or gastrointestinal tract in an outward direction (from the right to the left in FIG. 5) in a state in which the snare unit 300 is located inside the main body unit 100, to stably remove the object 5, such as a foreign substance or a temporarily inserted instrument, from the blood vessel or gastrointestinal tract.

The medical snare device 1 according to embodiments of the present disclosure may be provided with the plurality of support units 330, 330A, and 330B respectively connected to preset positions on the capture unit 310, such that the capture unit 310 may be stably positioned outside the object 5, such as a foreign object or a temporarily inserted instrument, and the object 5 may be accurately captured.

In addition, the capture unit 310 may be formed in a structure in which the plurality of arcs 311 are connected to each other such that the size of the capture unit 310 may be adjusted, for example, may be reduced, even inside the main body unit 100 or the guide unit 200 having a relatively small diameter, and even when the size of the entire capture unit 310 is reduced, its circular shape may be maintained due to the plurality of arcs 311, such that a shape necessary for capturing the object 5 may be implemented.

Figure 6:
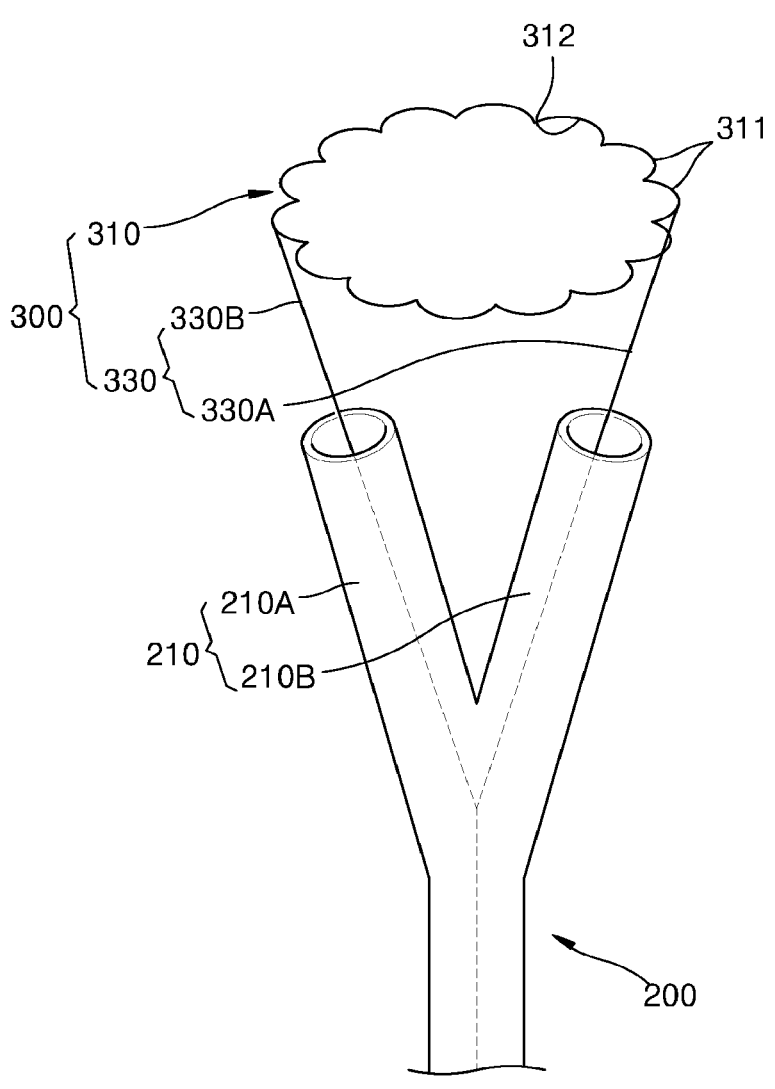
FIG. 6 is a diagram illustrating a medical snare device according to another embodiment of the present disclosure.

Hereinafter, the configuration, operation principle, and effects of a medical snare device according to another embodiment of the present disclosure will be described. FIG. 6 is a diagram illustrating a medical snare device according to another embodiment of the present disclosure.

Referring to FIG. 6, the medical snare device 1 according to another embodiment of the present disclosure may include a main body unit, the guide unit 200, and the snare unit 300.

Referring to FIG. 6, the guide unit 200 according to another embodiment of the present disclosure may include a guide bodies 210, 210A, and 210B. In detail, the guide unit 200 may include a plurality of guide bodies 210, 210A, and 210B to correspond to the plurality of support units 330, 330A, and 330B, respectively.

Referring to FIG. 6, the plurality of support units 330, 330A, 330B may be arranged inside the plurality of guide bodies 210, 210A, and 2106, respectively, and as the plurality of guide bodies 210, 210A, and 210B are formed, it is possible to stably guide moving paths of the support units 330, 330A, and 330B.

Referring to FIG. 6, the guide unit 200 according to another embodiment of the present disclosure may be formed in a single section, the plurality of guide bodies 210, 210A, and 210B may be formed in certain sections, and the plurality of support units 330, 330A, 330B may be arranged inside the plurality of guide bodies 210, 210A, and 210B, respectively.

However, the present disclosure is not limited thereto, and various modifications are possible, for example, a plurality of guide units 200 may be provided, and the plurality of support units 330, 330A, and 330B are movable inside the respective guide units 200 in the longitudinal direction.

Figure 7:
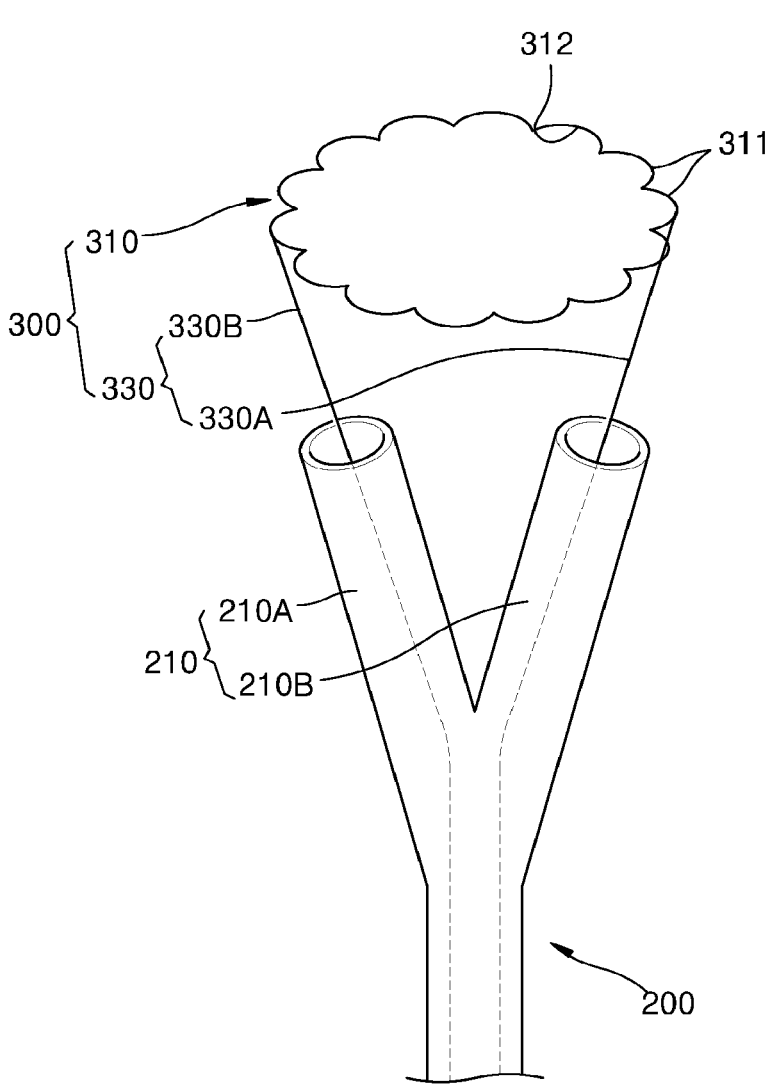
FIG. 7 is a diagram illustrating a medical snare device according to yet another embodiment of the present disclosure.

Referring to FIG. 6, the support units 330, 330A, and 330B may be integrally formed in a certain section, branch into a plurality of pieces after the section, and be connected to preset points on the capture unit 310, respectively. However, the present disclosure is not limited thereto, and as illustrated in FIG. 7, various modifications are possible, for example, a plurality of support units 330A and 330B may be continuously formed independently without a section in which they are integrally formed, in the longitudinal direction.

A medical snare device according to another embodiment of the present disclosure may be the same configuration, operation principle, and effects as those of the medical snare device 1 according to an embodiment of the present disclosure, except for including a plurality of guide bodies 210A and 210B such that a preset section of the guide unit 200 corresponds to the plurality of support units 330, 330A and 330B, and thus, detailed descriptions thereof will be omitted.

Particular executions described herein are merely examples and do not limit the scope of the present disclosure in any way. For the sake of brevity, conventional electronics, control systems, software and other functional aspects of the systems may not be described in detail. Furthermore, line connections or connection members between elements depicted in the drawings represent functional connections and/or physical or circuit connections by way of example, and in actual applications, they may be replaced or embodied with various suitable additional functional connections, physical connections, or circuit connections. Moreover, no item or component is essential to the practice of the present disclosure unless the item or component is specifically described as being "essential" or "critical".

Accordingly, the spirit of the present disclosure should not be limited to the above-described embodiments, and all modifications and variations which may be derived from the meanings, scopes and equivalents of the claims should be construed as failing within the scope of the present disclosure.

The invention claimed is:

1. A medical snare device comprising:

a main body unit that is open on both sides and has a hollow interior;

a guide unit that is relatively movable inside the main body unit and has a hollow interior; and a snare unit comprising a capture unit having a capture hole unit formed therein, and a plurality of support units that are relatively movable inside the guide unit and connected to the capture unit, wherein the plurality of support units are connected to preset points of the capture unit, respectively, and are arranged to face each other with respect to a center of the capture hole unit to apply a pulling force toward the guide unit, wherein the capture unit forms a single closed loop defining a perimeter of the capture hole unit, wherein the single closed loop comprises a plurality of arcs serially connected to one another end-to-end to form a continuous perimeter, wherein each of the plurality of arcs is convex in a direction radially outward from the center of the capture hole unit, wherein adjacent arcs of the plurality of arcs meet at a connection point, wherein each of the plurality of support units is fixedly coupled to a respective one of the connection points, wherein a distance from the connection point to the center of the capture hole unit is shorter than a distance from a center of each of the plurality of arcs to the center of the capture hole unit, and wherein a radius of curvature of each of the plurality of arcs is smaller than a radius of curvature of an imaginary circle connecting center points of the plurality of arcs.

2. The medical snare device of claim 1, wherein the plurality of support units are integrally formed in a preset section.

3. The medical snare device of claim 1, wherein the guide unit comprises a plurality of guide bodies that provide moving paths of the plurality of support units, respectively.

4. The medical snare device of claim 3, wherein the plurality of guide bodies are integrally formed in a preset section.

5. The medical snare device of claim 1, wherein the main body unit is formed of a polymer material.

6. The medical snare device of claim 1, wherein the plurality of support units are formed of a metal or polymer material.

\* \* \* \* \*